(12) United States Patent
Kurowski et al.

(10) Patent No.: US 10,733,903 B2
(45) Date of Patent: Aug. 4, 2020

(54) HEALTH AND WELLNESS MANAGEMENT METHODS AND SYSTEMS USEFUL FOR THE PRACTICE THEREOF

(71) Applicant: PATHWAY GENOMICS CORPORATION, San Diego, CA (US)

(72) Inventors: Scott J. Kurowski, San Diego, CA (US); Michael P. Nova, San Diego, CA (US)

(73) Assignee: Pathway Genomics Corporation, San Diego, CA (US)

(*) Notice: Subject to any disclaimer, the term of this patent is extended or adjusted under 35 U.S.C. 154(b) by 1235 days.

(21) Appl. No.: 14/829,426

(22) Filed: Aug. 18, 2015

(65) Prior Publication Data
US 2016/0071432 A1 Mar. 10, 2016

Related U.S. Application Data

(60) Provisional application No. 62/048,657, filed on Sep. 10, 2014.

(51) Int. Cl.
| | | |
|---|---|---|
| G09B 19/00 | (2006.01) | |
| G06F 19/00 | (2018.01) | |
| G16H 10/20 | (2018.01) | |
| A61B 5/01 | (2006.01) | |
| A61B 5/021 | (2006.01) | |
| A61B 5/08 | (2006.01) | |
| A61B 5/1172 | (2016.01) | |
| A61B 5/024 | (2006.01) | |

(Continued)

(52) U.S. Cl.
CPC ..... G09B 19/0092 (2013.01); G06F 19/3475 (2013.01); G16H 10/20 (2018.01); *A61B 5/0002* (2013.01); *A61B 5/01* (2013.01); *A61B 5/021* (2013.01); *A61B 5/024* (2013.01); *A61B 5/0816* (2013.01); *A61B 5/1172* (2013.01); *A61B 5/1176* (2013.01); *A61B 5/14532* (2013.01); *A61B 5/14542* (2013.01)

(58) Field of Classification Search
None
See application file for complete search history.

(56) References Cited

U.S. PATENT DOCUMENTS 7,953,613 B2   5/2011  Gizewski
8,690,578 B1 *  4/2014  Nusbaum ............... G09B 19/00
                                                   434/127

(Continued)

FOREIGN PATENT DOCUMENTS

JP   2010-170534 A   8/2010

OTHER PUBLICATIONS

International Search Report dated Oct. 29, 2015, for International Application No. PCT/US2015/045741, 17 pages.

(Continued)

*Primary Examiner* — Linh Giang Le
(74) *Attorney, Agent, or Firm* — Workman Nydegger

(57) ABSTRACT

In accordance with the present invention, there are provided health and wellness management methods which generate an action plan set of recommendations by taking into account a wide variety of inputs, including subject-specific information and globally applicable information. Also provided herewith are systems for the practice of the above-described methods.

4 Claims, 2 Drawing Sheets

(51) Int. Cl.
  *A61B 5/145*    (2006.01)
  *A61B 5/1171*   (2016.01)
  *A61B 5/00*     (2006.01)

(56)            References Cited

U.S. PATENT DOCUMENTS

2009/0254376 A1    10/2009   Martinez et al.
2011/0054934 A1     3/2011   Vesto
2012/0245435 A1     9/2012   Corpier et al.
2013/0138447 A1*    5/2013   Nova .................... G16B 50/00
                                                    705/2
2013/0151270 A1     6/2013   Nova et al.
2014/0088995 A1     3/2014   Damani
2014/0122109 A1*    5/2014   Ghanbari ............... G06F 19/00
                                                    705/2

OTHER PUBLICATIONS

Extended European Search Report dated Feb. 28, 2018, issued in EP Application No. 15840469.9.

\* cited by examiner

HEALTH AND WELLNESS MANAGEMENT METHODS AND SYSTEMS USEFUL FOR THE PRACTICE THEREOF

FIELD OF THE INVENTION

The present disclosure relates to health and wellness management methods and systems useful for the practice thereof.

BACKGROUND OF THE INVENTION

The information provided herein and references cited are provided solely to assist the understanding of the reader, and does not constitute an admission that any of the references or information is prior art to the present invention.

US Pub. No. US 2013/0138447 describes apparatus and methods to receive genetic material from a human test subject and characterize that genetic material into an electronic representation of a genome. Based upon the presence of certain genetic features, genetic markers or polymorphisms, a rules based logic path is executed to arrive at an action plan set of recommendations.

US Pub. No. US 2013/0151270 describes systems devised for health management based upon genetic markers.

SUMMARY OF THE INVENTION

In accordance with the present invention, there are provided health and wellness management methods which generate an action plan set of recommendations (and/or initiate personalized health and wellness actions (e.g., scheduling an appointment, when warranted, with a physician, an urgent care center, a hospital emergency room, and the like) by taking into account a wide variety of inputs, including subject-specific ("personalized") information and globally-applicable information. Also provided herewith are systems which facilitate the practice of the above-described methods.

In certain aspects and embodiments as described herein, the inputs contemplated include one or more of environmental information, family medical history information, micro biome sequence information, drug interaction information, nutritional information, exercise information, geographic data, climate data, meteorological data, retail data, pharmacy data, food and activity data, insurance data, market data, encyclopedias, scientific- and medical-related periodicals and journals, business information, research studies data, scientifically-curated genetics-related information, and the like.

In certain aspects and embodiments, the inputs include one or more of genomic information, phenotypic information, biochemical information, metabolic information, electronic medical record data, electronic health record data, drug prescriptions, biometric data, micro biome sequence information, the results of a family health history survey, in-application written chat logs, information regarding the subject's personal health care provider, information regarding the subject's insurance provider, patients advocate network information, social network information, and the like. In certain aspects and embodiments, the inputs include a plurality of the above-referenced datasets.

In certain aspects and embodiments, the inputs contemplated include a plurality of environmental information, family medical history information, drug interaction information, nutritional information, exercise information, micro biome sequence information, geographic data, climate data, meteorological data, retail data, pharmacy data, insurance data, market data, encyclopedias, scientific- and medical-related periodicals and journals, business information, research studies data, scientifically-curated genetics-related information, and the like.

In certain aspects and embodiments, the inputs contemplated include a plurality of genomic information, phenotypic information, biochemical information, metabolic information, micro biome sequence information, electronic medical record data, electronic health record data, drug prescriptions, biometric data, the results of a family health history survey, in-application written chat logs, information regarding the subject's personal health care provider, information regarding the subject's insurance provider, patients advocate network information, social network information, and the like.

In certain aspects and embodiments, the inputs contemplated include a plurality of environmental information, drug interaction information, geographic data, climate data, meteorological data, retail data, pharmacy data, food and activity data, insurance data, market data, encyclopedias, scientific- and medical-related periodicals and journals, business information, research studies data, scientifically-curated genetics-related information, genomic information, phenotypic information, biochemical information, metabolic information, electronic medical record data, electronic health record data, drug prescriptions, biometric data, micro biome sequence information, the results of a family health history survey, in-application written chat logs, information regarding the subject's personal health care provider, information regarding the subject's insurance provider, and the like.

In certain aspects and embodiments, the inputs contemplated include data from one or more images such as images of food, food containers, nutrition labels, plants, insects, medication, x-rays, labels, and the like. The image inputs may be processed using image recognition technology. The image recognition technology may be facial recognition, optical character recognition, pattern recognition, or the like.

As readily recognized by those of skill in the art, two or more of the above-described inputs can be employed to generate an action plan set of recommendations (and/or initiate personalized health and wellness action(s) (e.g., scheduling an appointment, when warranted, with a physician, an urgent care center, a hospital emergency room, and the like); in some embodiments, three or more of the above-described inputs can be employed to generate an action plan set of recommendations (and/or initiate personalized health and wellness action(s) as described herein); in some embodiments, four or more of the above-described inputs can be employed to generate an action plan set of recommendations (and/or initiate personalized health and wellness action(s) as described herein); in some embodiments, five or more of the above-described inputs can be employed to generate an action plan set of recommendations (and/or initiate personalized health and wellness action(s) as described herein); in some embodiments, six or more of the above-described inputs can be employed to generate an action plan set of recommendations (and/or initiate personalized health and wellness action(s) as described herein); in some embodiments, seven or more of the above-described inputs can be employed to generate an action plan set of recommendations (and/or initiate personalized health and wellness action(s) as described herein); in some embodiments, eight or more of the above-described inputs can be employed to generate an action plan set of recommendations (and/or initiate personalized health and wellness action(s) as described herein); in some embodiments, nine or more of the above-described inputs can be employed to generate an action plan set of recommendations (and/or initiate personalized health and wellness action(s) as described herein); in some embodiments, 10 or more of the above-described inputs can be employed to generate an action plan set of recommendations (and/or initiate personalized health and wellness action(s) as described herein); in some embodiments, 11 or more of the above-described inputs can be employed to generate an action plan set of recommendations (and/or initiate personalized health and wellness action(s) as described herein); in some embodiments, 12 or more of the above-described inputs can be employed to generate an action plan set of recommendations (and/or initiate personalized health and wellness action(s) as described herein); in some embodiments, 13 or more of the above-described inputs can be employed to generate an action plan set of recommendations (and/or initiate personalized health and wellness action(s) as described herein); in some embodiments, 14 or more of the above-described inputs can be employed to generate an action plan set of recommendations (and/or initiate personalized health and wellness action(s) as described herein); in some embodiments, 15 or more of the above-described inputs can be employed to generate an action plan set of recommendations (and/or initiate personalized health and wellness action(s) as described herein); in some embodiments, 16 or more of the above-described inputs can be employed to generate an action plan set of recommendations (and/or initiate personalized health and wellness action(s) as described herein); in some embodiments, 17 or more of the above-described inputs can be employed to generate an action plan set of recommendations (and/or initiate personalized health and wellness action(s) as described herein); in some embodiments, 18 or more of the above-described inputs can be employed to generate an action plan set of recommendations (and/or initiate personalized health and wellness action(s) as described herein); in some embodiments, 19 or more of the above-described inputs can be employed to generate an action plan set of recommendations (and/or initiate personalized health and wellness action(s) as described herein); in some embodiments, or 20 or more of the above-described inputs can be employed to generate an action plan set of recommendations (and/or initiate personalized health and wellness action(s) as described herein).

In certain aspects and embodiments, the inputs may be of a heterogeneous nature, such that they would not typically be associated or analyzed together. For example, for an input or query like "cytoskeleton-dependent intracellular transport", a number of datasets may be relevant, including the amino acid sequence of the protein encoded by the gene, the inferred evolutionary relationships of that protein to other proteins across various species, the microarray or RNA sequence expression profile of the gene across various phenotypes or environmental conditions, the number and identity of neighboring proteins, and the like. One of skill in the art will appreciate that such data sets are difficult to analyse jointly because of their heterogeneity.

A patient or subject for whom the invention methods can be employed to develop an action plan set of recommendations (and/or initiate personalized health and wellness action(s) as described herein) can mean either a human or a non-human animal. In an embodiment, the present disclosure provides methods for developing an action plan set of recommendations (and/or initiate personalized health and wellness action(s) as described herein) for the treatment of a human patient in need thereof. In an embodiment, the present disclosure provides methods for identifying suitable treatment or actionable recommendations (and/or initiating personalized health and wellness action(s) as described herein) for a human patient in need thereof. In another embodiment, the present disclosure provides methods for identifying suitable treatment of a veterinary patient in need thereof, including, but not limited to dogs, horses, cats, rabbits, gerbils, hamsters, rodents, birds, aquatic mammals, cattle, pigs, camelids, and other zoological animals.

The term "treating" refers to preventing a disease, disorder or condition from occurring in a cell, a tissue, a system, animal or human which may be predisposed to the disease, disorder and/or condition but has not yet been diagnosed as having it; stabilizing a disease, disorder or condition, i.e., arresting its development; and/or relieving one or more symptoms of the disease, disorder or condition, i.e., causing regression of the disease, disorder and/or condition. Treating also refers to managing a chronic condition, enhancing a patient's personal lifestyle traits with actionable recommendations (e.g., "run 2 miles today" or "eat some kale this morning"), and the like.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

Diseases, disorders and conditions of interest contemplated for managing in accordance with the present invention include one or more of the subject's measurable biological data. Exemplary measurable biological data include the subject's blood pressure, heart rate, temperature, respiration rate, blood sugar, cholesterol, blood oxygen levels, blood urea nitrogen (BUN), creatinine, HGA1C, C Reactive Protein (CRP), Tumor biomarker/Tumor DNA, and/or Circulating DNA/RNA, inflammatory markers, diseased cells, diseased organs, diseased tissue, or diseased multi-cellular organisms. Such diseases can include, for example, schizophrenia, bipolar disorder, major depression, ADHD, autism obsessive-compulsive disorder, substance abuse, Alzheimer's disease, Mild Cognitive impairment, Parkinson's disease, stroke, vascular dementia, Huntington's disease, epilepsy and Down syndrome. A diseased state could also include, for example, a diseased protein or a diseased process, such as defects in receptor signaling, neuronal firing, and cell signaling, which may occur in several different organs.

BRIEF DESCRIPTION OF THE FIGURES

FIG. 1 is a streamlined schematic representation of exemplary components of invention systems, illustrating the various inputs and outputs thereof, wherein:

Q=query from user.
V=secure private data vault.
R=private health reports and records, from various sources (including Pathway Genomics Corporation's genetics & genomics lab).
S=survey/chat log data from user, saved in vault V with R from various report and records sources.
L='lensed' (personalized) context data merged from vault V.
Q'(L)=user query, rewritten/modifed/data-augmented by Pathway Genomics Corporation's servers and annotated with L.

d1=expert-trained database & documents set 1 (e.g., genetics, business locations, and the like).
d2=expert-trained database & documents set 2 (e.g., medical procedures, insurance data, and the like).
dN=expert-trained database & documents set N (arbitrary count N, other data sources, and the like).
C=device application display directive/command.
A=NLP AI response/answer.
A'(C)=NLP AI response/answer, rewritten/modifed/data-augmented by Pathway Genomics Corporation's servers and annotated with C.

Figure 1:
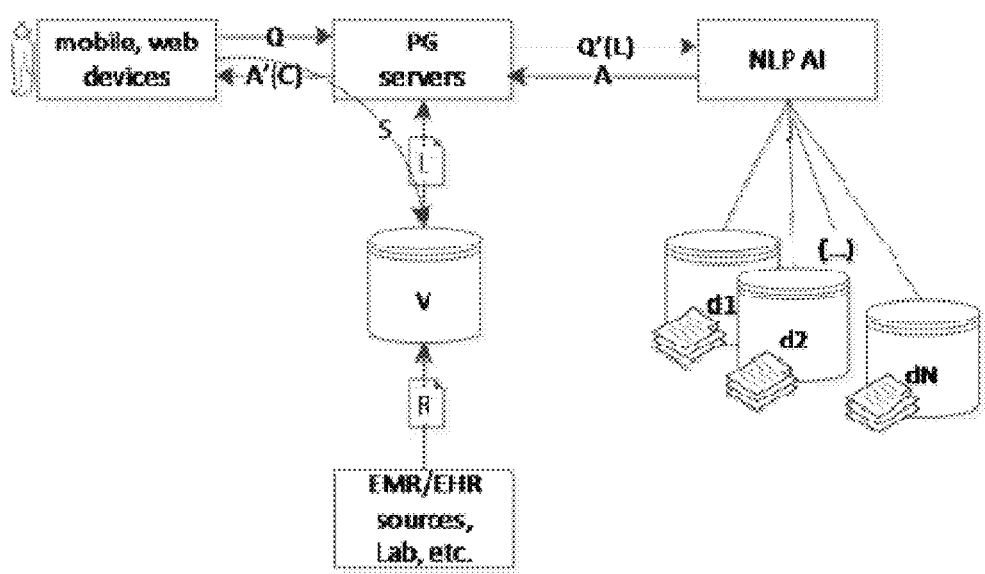
Figure 2:
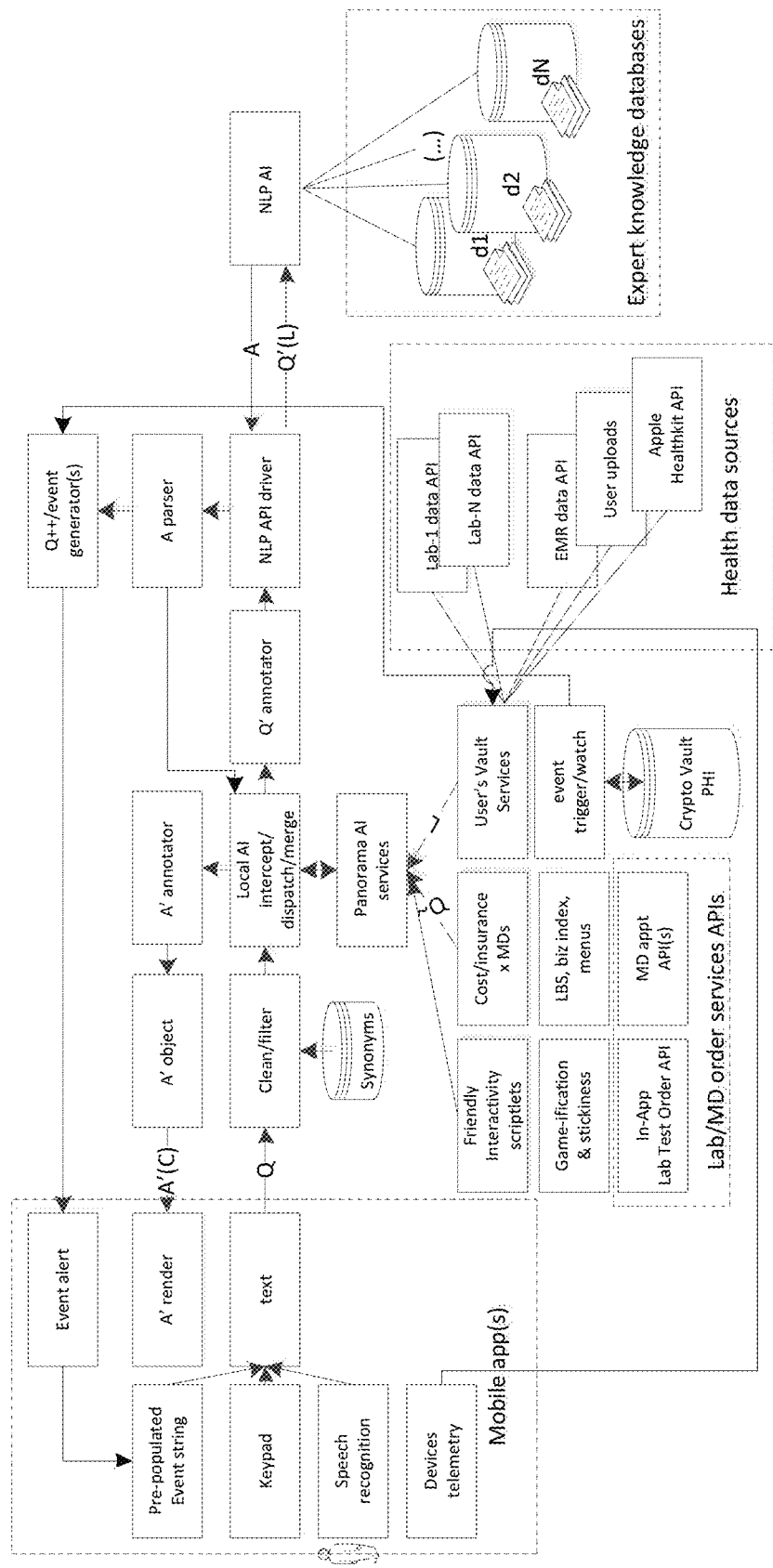

FIG. 2 is an expanded schematic representation of exemplary components of invention systems, illustrating the various inputs and outputs thereof, wherein the abbreviations used therein are the same as described in reference to FIG. 1. In the figure, the 2 boxes labeled "local AI intercept/dispatch/merge" and "OME AI services" taken together are sometimes referred to as the forebrain of the system.

As used herein, a "forebrain" is defined as an area that helps focus/lens or manage the data before interaction with AI. An example of the function of the forebrain would be the lensing data merge, where the user input is analyzed to determine what 'L' information to pull from the user's vault, auto-formulated for the NLP AI and merged, the result is then sent forward to the NLP AI, which receives the reply and applies QC filters, an audience selection filter, possibly prunes or replaces data with further inputs from local services, and finally returns that to the user for mobile presentation.

Another example of the function of the forebrain is when the user is just interacting casually—the OME AI 'forebrain' in this case determines that there is no context in a particular question relevant to the NLP AI at all, and routes it to its Friendly Interactivity Scriplets module for a typical or natural response to the user.

DETAILED DESCRIPTION OF THE PREFERRED EMBODIMENTS

In accordance with the present invention, there is provided an artificial intelligence system giving personalized health and wellness recommendations (and/or initiating personalized health and wellness actions (e.g., scheduling an appointment, when warranted, with a physician, an urgent care center, a hospital emergency room, and the like) for a human (or other animal) user.

In accordance with an embodiment of the invention, there are provided health and wellness management methods comprising
   (a) querying:
      at least one composite dataset, and
      at least one subject-specific dataset
      for information relevant to a condition or objective of interest,
   (b) analyzing the information retrieved in the preceding step, and
   (c) generating an observable response (e.g., written, spoken, visual, tactile, and the like) providing one or more possible further insight(s) and/or recommended course(s) of action to said subject and/or initiating personalized health and wellness actions (e.g., scheduling an appointment, when warranted, with a physician, an urgent care center, a hospital emergency room, and the like).

In the interest of providing a user with prompt guidance as to possible activity choice(s), certain of the information conveyed by way of the observable response will be pushed to the user, without the need for an initiating query; for example, if a subject is observed to have relocated to a new GPS location, where the subject will be exposed to substantially different environmental conditions (especially environmental conditions for which it has already been established that the subject is susceptible), the invention system will generate an alert that alternate activities and/or medical intervention may be warranted. In the event medical intervention may be warranted, the invention method may further include the step of scheduling an appointment with a physician, an urgent care center, a hospital emergency room, and the like.

In accordance with another embodiment of the invention, there are provided health and wellness management methods comprising
   (a) querying:
      a plurality of composite datasets, and
      optionally, at least one subject-specific dataset
      for information relevant to a condition or objective of interest,
   (b) analyzing the information retrieved in the preceding step, and
   (c) generating an observable response (e.g., written, spoken, visual, tactile, and the like) providing one or more possible further insight(s) and/or recommended course(s) of action to said subject and/or initiating personalized health and wellness actions (e.g., scheduling an appointment, when warranted, with a physician, an urgent care center, a hospital emergency room, and the like).

In the interest of providing a user with prompt guidance as to possible activity choice(s), certain of the information conveyed by way of the observable response will be pushed to the user, without the need for an initiating query; for example, if a subject is observed to have relocated to a new GPS location, where the subject will be exposed to substantially different environmental conditions (especially environmental conditions for which it has already been established that the subject is susceptible), the invention system will generate an alert that alternate activities and/or medical intervention may be warranted. In the event medical intervention may be warranted, the invention method may further include the step of scheduling an appointment with a physician, an urgent care center, a hospital emergency room, and the like.

The datasets contemplated for querying herein may be housed on the user's personal device, on a central server, on a server or servers connected through a communication network such as the internet, an intranet, a local area network (LAN), a wide area network (WAN), or the like.

As used herein, the term "composite dataset" refers to data collections that are not subject specific, i.e., data collections based on population-wide observations, local, regional or super-regional observations, and the like. Exemplary composite datasets include environmental information, drug interaction information, geographic data, climate data, meteorological data, retail data, pharmacy data, insurance data, market data, encyclopedias, scientific- and medical-related periodicals and journals, business information, research studies data, scientifically-curated genetics-related information, nutritional data, exercise data, physician and hospital/clinic location information, physician billing information, physician re-imbursement information, restaurant and grocery store location information, and the like.

In some embodiments, one or more of the composite datasets are routinely updated and/or supplemented.

In some embodiments, one or more datasets are added to the plurality of composite datasets.

As used herein, "environmental information" refers to a list of common allergens in a GPS region, pollen count, mold distribution, atmospheric particle count, infectious disease information, and the like. As noted above, in the interest of providing a user with prompt guidance as to possible activity choice(s), certain environmental information is pushed to the user, without the need for an initiating query, especially where such information indicates that the subject is located at a GPS location where the subject will be exposed to substantially different environmental conditions than in their normal home environment (especially environmental conditions for which it has already been established that the subject is susceptible), the invention system will generate an alert that alternate activities and/or medical intervention may be warranted. In the event medical intervention may be warranted, the invention method may further include the step of scheduling an appointment with a physician, an urgent care center, a hospital emergency room, and the like.

As used herein, "drug interaction information" refers to information regarding the likelihood that one drug may unfavorably interfere with the intended function of another.

As used herein, "geographic data" refers to current and historical GPS location(s) and/or street address(es) and/or postal zip code(s).

As used herein, "climate data" refers to the particular climate zone where one is located, climate data based on GPS location and date, and the like.

As used herein, "meteorological data" refers to such information as a link to the National Weather Service, air, water, snow temperatures, wind speed and direction, barometric data, wind chill, water vapor, altitude, humidity, dewpoint, weather forecast, aviation, tides, surf and diving conditions, and the like.

As used herein, "retail data" refers to the location of retail and professional services (including health-related care and therapeutic services), buying preferences, products and services and the cost thereof, and the like.

As used herein, "pharmacy data" refers to the location of a drug store, the availability and/or price of a prescription or medication, the availability of chiropractic, therapeutic and massage services, the location of medical services, the location of dental services, the location of clinical services, the location of lab services, the location of therapy services, the location of hospital services, and the like.

As used herein, "food and activity data" refers to the location of markets of interest (e.g., supermarkets, farmer's markets, and the like), the location of restaurants of interest, the location and identity of events of interest, the location of entertainment of interest, the location of exercise facilities, the location of exercise and/or restaurant chains, and the like.

As used herein, the phrase "insurance data" refers to the scope of coverage available under a given policy, the criteria for submitting a claim, the protocol for submitting a claim, claim history, the means to initiate pursuing pre-authorization for certain medication and/or medical procedures once the need for such medication and/or medical procedures has been identified, and the like.

As used herein, the phrase "market data" refers to sales information, target audience for a given product, product availability, present or upcoming promotions, commodities prices and volumes, and the like.

As used herein, the term "encyclopedias" refers to scholarly collections of information on a broad range of topics, whether in-print or available digitally, e.g., via the internet.

As used herein, reference to "scientific- and medical-related periodicals and journals" embraces all (refereed or non-refereed) publications which relate to studies and developments in the fields of human nutrition, human physiology, medical technology, and the like.

As used herein, the term "business information" refers to sales data, product information, availability of competitive products and/or services, and the like.

As used herein, the phrase "research studies data" refers to research results obtained from pre-clinical studies, clinical studies, post-clinical studies, and the like.

As used herein, the phrase "scientifically-curated genetics-related information" refers to correlations which have been established associating certain genetic irregularities with defined diseases or conditions.

As used herein, "nutritional data" refers to the nutritional content of various consumables, e.g., the content (and percent of recommended daily allowance) of various nutrients of interest, such as vitamin C, vitamin D, vitamin E, vitamin K, calcium, phosphorus, magnesium, manganese, iron, and the like.

As used herein, "exercise data" can refer to both subject-specific information, and globally-applicable information. For example, globally-applicable exercise data embraces information regarding which exercise(s) are indicated for strengthening certain muscle groups, which exercises are indicated for stretching certain joints, and the like; while subject specific exercise data may refer to the specific exercise(s) or exercise protocol engaged in by the subject, the intensity of such exercise, the duration of such exercise, and the like.

As used herein, "physician and hospital/clinic location information" refers to dataset(s) that identify the location of physicians, hospitals and/or clinics within a defined radius of the subject's position, so as to be readily accessible by the subject.

As used herein, "physician billing information" refers to both subject-specific information, and globally-applicable information. For example, globally-applicable information relates to average or typical charges asserted by a physician who practices in the relevant specialty and locale, whereas subject specific billing data refers to the charges asserted by a specific physician for a defined protocol.

As used herein, "physician re-imbursement information" refers to the average or typical charges for which a physician who practices in the relevant specialty and locale is typically reimbursed.

As used herein, "restaurant and grocery store location information" refers to dataset(s) that identify the location of restaurants, grocery stores, markets, and the like, within a defined radius of the subject's position, so as to be readily accessible by the subject.

As used herein, the term "subject-specific dataset" refers to a variety of information which is unique to each individual, such as, for example, genomic information, phenotypic information, biochemical information, metabolic information, micro biome sequence information, electronic medical record data, electronic health record data, drug prescriptions, biometric data, nutritional information, exercise information, family medical history information (e.g., as may be obtained via a family health history survey), in-application written chat logs, the subject's personal health care provider records and notes, the subject's insurance provider, patients advocate network information, social network information, and the like.

In some embodiments, one or more of the subject specific datasets are routinely updated and/or supplemented.

In some embodiments, one or more datasets are added to the plurality of subject-specific datasets.

As used herein, the phrase "subject-specific genomic information" refers to the genetic makeup of an individual, including mutations (SNPs, Del/Dups, VUS, etc.) and mutation frequencies, familial genome sequence information, structural genomic information (including mutations (sequence, deletion, insertions)), single nucleotide polymorphism, personal immunomics information (i.e., the study of immune system regulation and response to pathogens using genome-wide approaches), functional genomic information (functional genomics focuses on the dynamic aspects such as gene transcription, translation, and protein-protein interactions), computational genomic information (the use of computational and statistical analysis to decipher, discover or predict biology from genome sequences and related data), epigenomics (reversible modifications of DNA or histones that affect gene expression without altering the DNA sequence (e.g. DNA methylation and histone modification)), pathogenomics information including personal genome-microbe interactions involved in disease states, regenomic information, behavior genomic information, metagenomics (i.e., personal genetic material recovered directly from environmental samples; also known as as environmental genomics, ecogenomics or community genomics).

As used herein, "subject-specific phenotypic information" refers to gender, race, height, weight, hair color, eye color, heart rate, taste preference, blood pressure, self described medical symptoms, medically diagnosed symptoms, test results and/or diagnosis provided by medical professional, proteomic profile, and the like.

As used herein, "subject-specific biochemical information" refers to the results of clinical tests (e.g., sodium, magnesium, potassium, iron, blood urea nitrogen (BUN), uric acid, and the like), drug/medication levels in tissues, blood, etc.

As used herein, "subject-specific metabolic information" refers to the results of clinical enzyme and protein tests (such as, for example, Alanine Aminotransferase (ALT), Asparate Aminotransferase (AST), Creatinine (Cr), Creatine Kinase (CK), Lactate dehydrogenase (LDH), Myoglobin (Mb), Troponin T (cTNT), Complete Blood Count with Differential (CBC), Fasting blood sugar (FBS), Glycosylated Hemoglobin or Hemoglobin A1C (HBA1C), Lipoprotein a (Lp(a)), Apolipoprotein B (ApoB), Fibrinogen, N-terminal-pro-B-Type Natriuretic Peptide (NT-proBNP), LDL-associated PLA2 (PLAC), Urine Albumin/Creatinine ration (Ualb/Cr), Global Risk Score (GRS), Cholesterol, Low Density Lipoprotein (LDL), High Density Lipoprotein (HDL), Triglycerides (TG), Thyroid Simulating Hormone (TSH), Microsomal Thyroid Antibodies (TPO), Tyroxine T4, and the like.

As used herein, "micro biome sequence information" refers to nucleotide sequence information obtained from the ecological community of commensal, symbiotic, and pathogenic microorganisms that literally share our body space.

As used herein, the terms "subject-specific Electronic medical record data" (EMR), "Electronic Health Records" (EHR), and "Personal Health Records" (PHRs) refer to medical and clinical data from individual health care providers, clinics, hospitals, care facilities, subject health history, subject predisposition to disease, subject medical history, diagnoses, medication/perscriptions, treatment plans, immunization dates, allergies, radiology images, laboratory and test results, advance directives, biopsies, data from home and mobile monitoring devices such as FITBIT, iWatch, Withings scale, wireless blood pressure cuff, etc., and the like.

As used herein, the term "drug prescriptions" refers to all drugs which have been prescribed specifically for the individual seeking to employ the invention health and wellness management methods.

As used herein, "subject-specific biometric data" refers to both physical biometrics and behaviorial biometrics.

Examples of physical biometrics include fingerprints, palm prints, hand geometry, facial recognition, iris recognition, voice print, wrist vein recognition, retinal recognition, electroencephalogram, electrocardiogram, pulse, blood pressure, heart rate, temperature, respiration rate, body mass index (BMI), blood sugar, cholesterol, blood oxygen levels, blood urea nitrogen (BUN), creatinine, HGA1C, C Reactive Protein (CRP), Tumor biomarker/Tumor DNA, and/or Circulating DNA/RNA, or other health problem, fitness objective or wellness goal, and the like.

Examples of behaviorial biometrics include specific mannerisms or physical characteristics, biometric motion accelerometer data (movement), biometric data (such as blood pressure, heart rate, etc.), biomarker data (such as HgA1C, Glucose, etc.), and the like.

As used herein, "subject-specific nutritional information" refers to the nutritional requirements of the subject, e.g., the need for supplementation with various nutrients of interest, such as vitamin C, vitamin D, vitamin E, vitamin K, calcium, phosphorus, magnesium, manganese, iron, and the like.

As used herein, "subject-specific exercise information" refers to the specific exercise(s) or exercise protocol engaged in by the subject, the intensity of such exercise, the duration of such exercise, and the like.

As used herein, the phrase "family medical history information", such as may be obtained using a family health history survey, refers to all relevant health information with respect to one's immediate family, such as the occurrence of significant health issues such as heart disease, diabetes, high blood pressure, high cholesterol, and the like.

As used herein, the phrase "in-application written chat logs" refers to random information provided by the subject during the use of the invention methods, e.g., random comments regarding various symptoms such as pain, shortness of breath, and the like.

As used herein, the phrase "personal health care provider" refers to the medical treatment team on whom the individual seeking to employ the invention health and wellness management methods relies.

As used herein, the term "insurance provider" refers to the specific insurance carrier from whom the individual seeking to employ the invention health and wellness management methods obtains their insurance coverage.

As used herein, "patients advocate network information" refers to information of general applicability to anyone diagnosed with a defined disease or condition.

As used herein, "social network information" refers to the collective wisdom elicited on behalf of the subject from members of their social network.

In some embodiments of the invention at least one member of the composite dataset, and at least one member of the subject-specific dataset is queried.

In some embodiments of the invention a plurality of members of the composite dataset, and at least one member of the subject-specific dataset are queried.

In some embodiments of the invention at least one member of the composite dataset, and a plurality of members of the subject-specific dataset are queried.

In some embodiments of the invention a plurality of members of the composite dataset, and a plurality of members of the subject-specific dataset are queried.

In some embodiments of the invention, the subject-specific dataset queried is at least the genomic information, and the composite dataset queried is at least environmental information.

In some embodiments of the invention, the subject-specific dataset queried is at least the genomic information, and the composite dataset queried is at least drug interaction information.

In some embodiments of the invention, the subject-specific dataset queried is at least the genomic information, and the composite dataset queried is at least geographic data.

In some embodiments of the invention, the subject-specific dataset queried is at least the genomic information, and the composite dataset queried is at least climate data.

In some embodiments of the invention, the subject-specific dataset queried is at least the genomic information, and the composite dataset queried is at least meteorological data.

In some embodiments of the invention, the subject-specific dataset queried is at least the genomic information, and the composite dataset queried is at least retail data.

In some embodiments of the invention, the subject-specific dataset queried is at least the genomic information, and the composite dataset queried is at least insurance data.

In some embodiments of the invention, the subject-specific dataset queried is at least the genomic information, and the composite dataset queried is at least market data.

In some embodiments of the invention, the subject-specific dataset queried is at least the genomic information, and the composite dataset queried is at least encyclopedias.

In some embodiments of the invention, the subject-specific dataset queried is at least the genomic information, and the composite dataset queried is at least scientific- and medical-related periodicals and journals.

In some embodiments of the invention, the subject-specific dataset queried is at least the genomic information, and the composite dataset queried is at least business information.

In some embodiments of the invention, the subject-specific dataset queried is at least the genomic information, and the composite dataset queried is at least research studies data.

In some embodiments of the invention, the subject-specific dataset queried is at least the genomic information, and the composite dataset queried is at least scientifically-curated genetics-related information.

In some embodiments of the invention, the subject-specific dataset queried is at least the phenotypic information, and the composite dataset queried is at least environmental information.

In some embodiments of the invention, the subject-specific dataset queried is at least the phenotypic information, and the composite dataset queried is at least drug interaction information.

In some embodiments of the invention, the subject-specific dataset queried is at least the phenotypic information, and the composite dataset queried is at least geographic data.

In some embodiments of the invention, the subject-specific dataset queried is at least the phenotypic information, and the composite dataset queried is at least climate data.

In some embodiments of the invention, the subject-specific dataset queried is at least the phenotypic information, and the composite dataset queried is at least meteorological data.

In some embodiments of the invention, the subject-specific dataset queried is at least the phenotypic information, and the composite dataset queried is at least retail data.

In some embodiments of the invention, the subject-specific dataset queried is at least the phenotypic information, and the composite dataset queried is at least insurance data.

In some embodiments of the invention, the subject-specific dataset queried is at least the phenotypic information, and the composite dataset queried is at least market data.

In some embodiments of the invention, the subject-specific dataset queried is at least the phenotypic information, and the composite dataset queried is at least encyclopedias.

In some embodiments of the invention, the subject-specific dataset queried is at least the phenotypic information, and the composite dataset queried is at least scientific- and medical-related periodicals and journals.

In some embodiments of the invention, the subject-specific dataset queried is at least the phenotypic information, and the composite dataset queried is at least business information.

In some embodiments of the invention, the subject-specific dataset queried is at least the phenotypic information, and the composite dataset queried is at least research studies data.

In some embodiments of the invention, the subject-specific dataset queried is at least the phenotypic information, and the composite dataset queried is at least scientifically-curated genetics-related information.

In some embodiments of the invention, the subject-specific dataset queried is at least the biochemical information, and the composite dataset queried is at least environmental information.

In some embodiments of the invention, the subject-specific dataset queried is at least the biochemical information, and the composite dataset queried is at least drug interaction information.

In some embodiments of the invention, the subject-specific dataset queried is at least the biochemical information, and the composite dataset queried is at least geographic data.

In some embodiments of the invention, the subject-specific dataset queried is at least the biochemical information, and the composite dataset queried is at least climate data.

In some embodiments of the invention, the subject-specific dataset queried is at least the biochemical information, and the composite dataset queried is at least meteorological data.

In some embodiments of the invention, the subject-specific dataset queried is at least the biochemical information, and the composite dataset queried is at least retail data.

In some embodiments of the invention, the subject-specific dataset queried is at least the biochemical information, and the composite dataset queried is at least insurance data.

In some embodiments of the invention, the subject-specific dataset queried is at least the biochemical information, and the composite dataset queried is at least market data.

In some embodiments of the invention, the subject-specific dataset queried is at least the biochemical information, and the composite dataset queried is at least encyclopedias.

In some embodiments of the invention, the subject-specific dataset queried is at least the biochemical information, and the composite dataset queried is at least scientific- and medical-related periodicals and journals.

In some embodiments of the invention, the subject-specific dataset queried is at least the biochemical information, and the composite dataset queried is at least business information.

In some embodiments of the invention, the subject-specific dataset queried is at least the biochemical information, and the composite dataset queried is at least research studies data.

In some embodiments of the invention, the subject-specific dataset queried is at least the biochemical information, and the composite dataset queried is at least scientifically-curated genetics-related information.

In some embodiments of the invention, the subject-specific dataset queried is at least the metabolic information, and the composite dataset queried is at least environmental information.

In some embodiments of the invention, the subject-specific dataset queried is at least the metabolic information, and the composite dataset queried is at least drug interaction information.

In some embodiments of the invention, the subject-specific dataset queried is at least the metabolic information, and the composite dataset queried is at least geographic data.

In some embodiments of the invention, the subject-specific dataset queried is at least the metabolic information, and the composite dataset queried is at least climate data.

In some embodiments of the invention, the subject-specific dataset queried is at least the metabolic information, and the composite dataset queried is at least meteorological data.

In some embodiments of the invention, the subject-specific dataset queried is at least the metabolic information, and the composite dataset queried is at least retail data.

In some embodiments of the invention, the subject-specific dataset queried is at least the metabolic information, and the composite dataset queried is at least insurance data.

In some embodiments of the invention, the subject-specific dataset queried is at least the metabolic information, and the composite dataset queried is at least market data.

In some embodiments of the invention, the subject-specific dataset queried is at least the metabolic information, and the composite dataset queried is at least encyclopedias.

In some embodiments of the invention, the subject-specific dataset queried is at least the metabolic information, and the composite dataset queried is at least scientific- and medical-related periodicals and journals.

In some embodiments of the invention, the subject-specific dataset queried is at least the metabolic information, and the composite dataset queried is at least business information.

In some embodiments of the invention, the subject-specific dataset queried is at least the metabolic information, and the composite dataset queried is at least research studies data.

In some embodiments of the invention, the subject-specific dataset queried is at least the metabolic information, and the composite dataset queried is at least scientifically-curated genetics-related information.

In some embodiments of the invention, the subject-specific dataset queried is at least the micro biome sequence information, and the composite dataset queried is at least environmental information.

In some embodiments of the invention, the subject-specific dataset queried is at least the micro biome sequence information, and the composite dataset queried is at least drug interaction information.

In some embodiments of the invention, the subject-specific dataset queried is at least the micro biome sequence information, and the composite dataset queried is at least geographic data.

In some embodiments of the invention, the subject-specific dataset queried is at least the micro biome sequence information, and the composite dataset queried is at least climate data.

In some embodiments of the invention, the subject-specific dataset queried is at least the micro biome sequence information, and the composite dataset queried is at least meteorological data.

In some embodiments of the invention, the subject-specific dataset queried is at least the micro biome sequence information, and the composite dataset queried is at least retail data.

In some embodiments of the invention, the subject-specific dataset queried is at least the micro biome sequence information, and the composite dataset queried is at least insurance data.

In some embodiments of the invention, the subject-specific dataset queried is at least the micro biome sequence information, and the composite dataset queried is at least market data.

In some embodiments of the invention, the subject-specific dataset queried is at least the micro biome sequence information, and the composite dataset queried is at least encyclopedias.

In some embodiments of the invention, the subject-specific dataset queried is at least the micro biome sequence information, and the composite dataset queried is at least scientific- and medical-related periodicals and journals.

In some embodiments of the invention, the subject-specific dataset queried is at least the micro biome sequence information, and the composite dataset queried is at least business information.

In some embodiments of the invention, the subject-specific dataset queried is at least the micro biome sequence information, and the composite dataset queried is at least research studies data.

In some embodiments of the invention, the subject-specific dataset queried is at least the micro biome sequence information, and the composite dataset queried is at least scientifically-curated genetics-related information.

In some embodiments of the invention, the subject-specific dataset queried is at least the electronic medical record data, and the composite dataset queried is at least environmental information (preferably along with such subject-specific information as what a user ate, drank, etc., and what exercises the user undertook on a daily basis).

In some embodiments of the invention, the subject-specific dataset queried is at least the electronic medical record data, and the composite dataset queried is at least drug interaction information.

In some embodiments of the invention, the subject-specific dataset queried is at least the electronic medical record data, and the composite dataset queried is at least geographic data.

In some embodiments of the invention, the subject-specific dataset queried is at least the electronic medical record data, and the composite dataset queried is at least climate data.

In some embodiments of the invention, the subject-specific dataset queried is at least the electronic medical record data, and the composite dataset queried is at least meteorological data.

In some embodiments of the invention, the subject-specific dataset queried is at least the electronic medical record data, and the composite dataset queried is at least retail data.

In some embodiments of the invention, the subject-specific dataset queried is at least the electronic medical record data, and the composite dataset queried is at least insurance data.

In some embodiments of the invention, the subject-specific dataset queried is at least the electronic medical record data, and the composite dataset queried is at least market data.

In some embodiments of the invention, the subject-specific dataset queried is at least the electronic medical record data, and the composite dataset queried is at least encyclopedias.

In some embodiments of the invention, the subject-specific dataset queried is at least the electronic medical record data, and the composite dataset queried is at least scientific- and medical-related periodicals and journals.

In some embodiments of the invention, the subject-specific dataset queried is at least the electronic medical record data, and the composite dataset queried is at least business information.

In some embodiments of the invention, the subject-specific dataset queried is at least the electronic medical record data, and the composite dataset queried is at least research studies data.

In some embodiments of the invention, the subject-specific dataset queried is at least the electronic medical record data, and the composite dataset queried is at least scientifically-curated genetics-related information.

In some embodiments of the invention, the subject-specific dataset queried is at least the drug prescription data, and the composite dataset queried is at least environmental information.

In some embodiments of the invention, the subject-specific dataset queried is at least the drug prescription data, and the composite dataset queried is at least drug interaction information.

In some embodiments of the invention, the subject-specific dataset queried is at least the drug prescription data, and the composite dataset queried is at least geographic data.

In some embodiments of the invention, the subject-specific dataset queried is at least the drug prescription data, and the composite dataset queried is at least climate data.

In some embodiments of the invention, the subject-specific dataset queried is at least the drug prescription data, and the composite dataset queried is at least meteorological data.

In some embodiments of the invention, the subject-specific dataset queried is at least the drug prescription data, and the composite dataset queried is at least retail data.

In some embodiments of the invention, the subject-specific dataset queried is at least the drug prescription data, and the composite dataset queried is at least insurance data.

In some embodiments of the invention, the subject-specific dataset queried is at least the drug prescription data, and the composite dataset queried is at least market data.

In some embodiments of the invention, the subject-specific dataset queried is at least the drug prescription data, and the composite dataset queried is at least encyclopedias.

In some embodiments of the invention, the subject-specific dataset queried is at least the drug prescription data, and the composite dataset queried is at least scientific- and medical-related periodicals and journals.

In some embodiments of the invention, the subject-specific dataset queried is at least the drug prescription data, and the composite dataset queried is at least business information.

In some embodiments of the invention, the subject-specific dataset queried is at least the drug prescription data, and the composite dataset queried is at least research studies data.

In some embodiments of the invention, the subject-specific dataset queried is at least the drug prescription data, and the composite dataset queried is at least scientifically-curated genetics-related information.

In some embodiments of the invention, the subject-specific dataset queried is at least the biometric data dataset, and the composite dataset queried is at least environmental information.

In some embodiments of the invention, the subject-specific dataset queried is at least the biometric data dataset, and the composite dataset queried is at least drug interaction information.

In some embodiments of the invention, the subject-specific dataset queried is at least the biometric data dataset, and the composite dataset queried is at least geographic data.

In some embodiments of the invention, the subject-specific dataset queried is at least the biometric data dataset, and the composite dataset queried is at least climate data.

In some embodiments of the invention, the subject-specific dataset queried is at least the biometric data dataset, and the composite dataset queried is at least meteorological data.

In some embodiments of the invention, the subject-specific dataset queried is at least the biometric data dataset, and the composite dataset queried is at least retail data.

In some embodiments of the invention, the subject-specific dataset queried is at least the biometric data dataset, and the composite dataset queried is at least insurance data.

In some embodiments of the invention, the subject-specific dataset queried is at least the biometric data dataset, and the composite dataset queried is at least market data.

In some embodiments of the invention, the subject-specific dataset queried is at least the biometric data dataset, and the composite dataset queried is at least encyclopedias.

In some embodiments of the invention, the subject-specific dataset queried is at least the biometric data dataset, and the composite dataset queried is at least scientific- and medical-related periodicals and journals.

In some embodiments of the invention, the subject-specific dataset queried is at least the biometric data dataset, and the composite dataset queried is at least business information.

In some embodiments of the invention, the subject-specific dataset queried is at least the biometric data dataset, and the composite dataset queried is at least research studies data.

In some embodiments of the invention, the subject-specific dataset queried is at least the biometric data dataset, and the composite dataset queried is at least scientifically-curated genetics-related information.

As readily recognized by those of skill in the art, a plurality of the above-described inputs can be employed to generate an action plan set of recommendations; in some embodiments, three or more of the above-described inputs can be employed to generate an action plan set of recommendations; in some embodiments, four or more of the above-described inputs can be employed to generate an action plan set of recommendations; in some embodiments, five or more of the above-described inputs can be employed to generate an action plan set of recommendations; in some embodiments, six or more of the above-described inputs can be employed to generate an action plan set of recommendations; in some embodiments, seven or more of the above-described inputs can be employed to generate an action plan set of recommendations; in some embodiments, eight or more of the above-described inputs can be employed to generate an action plan set of recommendations; in some embodiments, nine or more of the above-described inputs can be employed to generate an action plan set of recommendations; in some embodiments, 10 or more of the above-described inputs can be employed to generate an action plan set of recommendations; in some embodiments, 11 or more of the above-described inputs can be employed to generate an action plan set of recommendations; in some embodiments, 12 or more of the above-described inputs can be employed to generate an action plan set of recommendations; in some embodiments, 13 or more of the above-described inputs can be employed to generate an action plan set of recommendations; in some embodiments, 14 or more of the above-described inputs can be employed to generate an action plan set of recommendations; in some embodiments, 15 or more of the above-described inputs can be employed to generate an action plan set of recommendations; in some embodiments, 16 or more of the above-described inputs can be employed to generate an action plan set of recommendations; in some embodiments, 17 or more of the above-described inputs can be employed to generate an action plan set of recommendations; in some embodiments, 18 or more of the above-described inputs can be employed to generate an action plan set of recommendations; in some embodiments, 19 or more of the above-described inputs can be employed to generate an action plan set of recommendations; in some embodiments, or 20 or more of the above-described inputs can be employed to generate an action plan set of recommendations.

The datasets contemplated for querying herein may be housed on the user's personal device, on a central server, on a server or servers connected through a communication network such as the internet, an intranet, a local area network (LAN), a wide area network (WAN), and the like.

The specific queries (and specific combination of inquiries) utilized will depend on the guidance sought by the user, the availability of relevant information, and the like. Exemplary queries include "Where can I get a healthy dinner tonight?"; "How much should I expect to pay for a knee replacement?"; "My husband has no genetic carrier mutations; will our children get sick with my mother's diseases?"; "Thus far today, I have consumed the following . . . what menu options for dinner will provide me with optimal protein, carbohydrate and fat consumption?"; "What should my menu preferences be for today?"; "What exercise(s) should I do today?"; "My hand is swollen, what should I do?"; "How do I manage my blood pressure?"; "How do I manage my heart rate?"; "How do I manage my temperature?"; "How do I manage my respiration rate?"; "How do I manage my blood sugar?"; "How do I manage my cholesterol levels?"; "How do I manage my blood oxygen levels?"; "How do I manage my blood urea nitrogen (BUN) levels?"; "How do I manage my creatinine levels?"; "How do I manage my HGA1C levels?"; "How do I manage my C Reactive Protein (CRP) levels?"; "How do I manage my Tumor biomarker/Tumor DNA, and/or Circulating DNA/RNA?"; "How do I manage my inflammatory markers?"; "How do I manage my diseased cells?"; "How do I manage my diseased organs?"; "How do I manage my diseased tissue?"; "How do I manage my schizophrenia?"; "How do I manage my bipolar disorder?"; "How do I manage my major depression?"; "How do I manage my ADHD?"; "How do I manage my autism obsessive-compulsive disorder?"; "How do I manage my substance abuse?"; "How do I manage my Alzheimer's disease?"; "How do I manage my Mild Cognitive impairment?"; "How do I manage my Parkinson's disease?"; "How do I manage my stroke?"; "How do I manage my vascular dementia?"; "How do I manage my Huntington's disease?"; "How do I manage my epilepsy?"; "How do I manage my Down syndrome?"; and the like.

The query contemplated to initiate the invention method can be a written and/or spoken query. In some embodiments, some written questions can be auto-generated by the method to guide the user's line of inquiry toward a specific answer. In some embodiments, the auto-generated questions are presented as touch-to-ask-this questions. In some embodiments, the query can be user-interactive.

In accordance with the present invention, the information retrieved in the querying step is analyzed by Natural Language Processing Artificial Intelligence (NLP AI) which operates upon the composite and subject-specific datasets to generate multiple hypotheses for both the natural human meaning of the query and answers to the query, and presents in descending sorted-order one or more confidence-scored answers extracted from the dataset(s), wherein the NLP AI has been trained by one or more subject-matter experts selected from the group consisting of scientists, doctors, nurses, researchers, and clinicians or the NLP AI is trained directly by the subject.

As used herein, "Natural Language Processing" (NLP) refers to the branch of computer science focused on developing systems that allow computers to communicate with people using everyday language. Artificial Intelligence refers to the ability of a computer system to emulate or reproduce human-like responses or behaviors to human interactions. An NLP AI combines these abilities.

In some embodiments of the present invention, the NLP AI may be queried either together with the context of the subject-specific dataset, or without it, where (a) the subject-specific dataset is automatically maintained within the user's personal data vault (see "V" of FIG. 1);

(b) the subject-specific dataset is automatically updated within the user's personal data vault, or may be manually updated with specific data transmitted directly from, or indirectly by authorized persons, with data from newly-released clinical laboratory test(s) (see "R" of FIG. 1), new or user-edited in-application chat log text entries (see "S" of FIG. 1), new medical records, medical information and/or user preference information; and (c) the contextual information (see "L" in FIG. 1) of the subject-specific dataset modifies with additional specificity and accuracy the response knowledge or actionable recommendations generated by the NLP AI.

Conditions of interest contemplated for managing in accordance with the present invention include one or more of the subject's measurable biological data. Exemplary measurable biological data include the subject's blood pressure, heart rate, temperature, respiration rate, blood sugar, cholesterol, blood oxygen levels, blood urea nitrogen (BUN), creatinine, HGA1C, C Reactive Protein (CRP), Tumor biomarker/Tumor DNA, and/or Circulating DNA/RNA, inflammatory markers, diseased cells, diseased organs, diseased tissue, or diseased multi-cellular organisms. Such diseases can include, for example, schizophrenia, bipolar disorder, major depression, ADHD, autism obsessive-compulsive disorder, substance abuse, Alzheimer's disease, Mild Cognitive impairment, Parkinson's disease, stroke, vascular dementia, Huntington's disease, epilepsy and Down syndrome. A disease state could also include, for example, a diseased protein or a diseased process, such as defects in receptor signaling, neuronal firing, and cell signaling, which may occur in several different organs, and the like.

In some embodiments of the present invention, the subject whose health is being managed has been diagnosed with a defined trait or condition, or may be curious as to whether they may be predisposed to said trait or condition.

In some embodiments of the present invention, the subject is pre-disposed to a defined condition, but does not yet manifest symptoms of said condition.

In some embodiments of the present invention, the objective of the subject whose health is being managed is to promote weight loss, reduce blood pressure, reduce heart rate, monitor respiration rate, reduce blood sugar, reduce cholesterol, improve blood oxygen levels, reduce blood urea nitrogen (BUN), reduce creatinine, reduce HGA1C, reduce C Reactive Protein (CRP), reduce Tumor biomarker/Tumor DNA, reduce Circulating DNA/RNA, reduce inflammatory markers, and the like.

In some embodiments, the observable response providing recommended further course of action to said subject can be delivered in written form, spoken form, visual form, tactile form, and the like. Said observable response can be delivered to said subject in a variety of ways, e.g., by screen display, printed output, text message, email, an audible reminder signal, buzzer, instant messaging, social media, message boards/blogs, or other suitable private or user-authorized public form of communication.

As readily recognized by those of skill in the art, a wide variety of further course(s) of action may be recommended. Exemplary recommended further course(s) of action include one or more of dietary changes, life style changes, therapeutic regimen, medication regimen, insurance coverage, doctor visit and scheduling, preventative medicine protocols, exercise regimen, social network contact, medical network contact, procedure price, retail purchasing information, food and restaurant information, behavioral changes, spa and gym locations, walking trains, biking trails, running trails, and the like.

In some embodiments of the present invention, recommended further course(s) of action may relate to activities and/or food options within close proximity to the subject, wherein said activities and/or food options are consistent with the further course(s) of action recommended for said subject. In some embodiments, the invention may further comprise booking a reservation for said recommended further course of action.

In accordance with another embodiment of the present invention, there are provided health and wellness management methods comprising
(a) querying:
at least one composite dataset, and
at least one subject-specific dataset
for information relevant to a condition or objective of interest, and
(b) generating an observable response providing one or more possible further insight(s) and/or recommended course(s) of action to said subject and/or initiating personalized health and wellness actions (e.g., scheduling an appointment, when warranted, with a physician, an urgent care center, a hospital emergency room, and the like) based on an analysis of the information retrieved in the querying step.

In accordance with another embodiment of the present invention, there are provided health and wellness management methods comprising
(a) querying:
a plurality of composite datasets, and
optionally, at least one subject-specific dataset
for information relevant to a condition or objective of interest, and
(b) generating an observable response providing one or more possible further insight(s) and/or recommended course(s) of action to said subject and/or initiating personalized health and wellness actions (e.g., scheduling an appointment, when warranted, with a physician, an urgent care center, a hospital emergency room, and the like) based on an analysis of the information retrieved in the querying step.

In accordance with still another embodiment of the present invention, there are provided wellness management methods comprising
(a) querying:
at least one composite dataset, and
at least one subject-specific dataset
for information relevant to an activity or objective of interest,
(b) analyzing the information retrieved in the preceding step, and
(c) generating an observable response providing one or more possible further insight(s) and/or recommended course(s) of action to substantially maintain the health and wellness status of said subject and/or initiating personalized health and wellness actions (e.g., scheduling an appointment, when warranted, with a physician, an urgent care center, a hospital emergency room, and the like).

In accordance with still another embodiment of the present invention, there are provided wellness management methods comprising
(a) querying:
a plurality of composite datasets, and
optionally, at least one subject-specific dataset
for information relevant to an activity or objective of interest,
(b) analyzing the information retrieved in the preceding step, and
(c) generating an observable response providing one or more possible further insight(s) and/or recommended course(s) of action to substantially maintain the health and wellness status of said subject and/or initiating personalized health and wellness actions (e.g., scheduling an appointment, when warranted, with a physician, an urgent care center, a hospital emergency room, and the like).

In accordance with yet another embodiment of the present invention, there are provided methods for guiding a consumer purchase, said methods comprising
(a) querying:
at least one composite dataset, and
at least one subject-specific dataset
for information relevant to a condition or objective of interest,
(b) analyzing the information retrieved in the preceding step to generate a consumer profile, and
(c) generating a recommended purchase based on said consumer profile.

In accordance with yet another embodiment of the present invention, there are provided methods for guiding a consumer purchase, said methods comprising (a) querying:
  a plurality of composite datasets, and
  optionally, at least one subject-specific dataset
    for information relevant to a condition or objective of interest,
(b) analyzing the information retrieved in the preceding step to generate a consumer profile, and
(c) generating a recommended purchase based on said consumer profile.

In accordance with still another embodiment of the present invention, there are provided health information vaults comprising a plurality of subject-specific datasets. Subject-specific datasets contemplated for inclusion in the subject-specific health information vaults include genomic information, phenotypic information, biochemical information, metabolic information, electronic medical record data, electronic health record data, drug prescriptions, biometric data, the results of a family health history survey, in-application written chat logs, and the like.

In accordance with a further embodiment of the present invention, there are provided health and wellness management systems comprising:
  a plurality of composite datasets,
  optionally, a plurality of subject-specific datasets,
  an NLP AI analysis module, and
  a user-interactive reporter functionality,
wherein:
  the analysis module is communicatively coupled to the plurality of composite datasets and the optional plurality of subject-specific datasets and arranged so as to couple appropriate inputs therefrom;
  the analysis module executes an algorithm which produces outputs based on the specific datasets which are queried, and
  the outputs are related to diet, exercise, nutrition, and/or medical intervention, and passes those outputs to the reporter functionality.

Such systems can be employed using only a plurality of composite datasets; alternatively, such systems can further comprise a plurality of subject-specific datasets.

In accordance with a still further embodiment of the present invention, there are provided apps which facilitate user-interactive querying of:
  at least one composite dataset, and
  optionally, at least one subject-specific dataset
  for information relevant to a condition or objective of interest, said app comprising:
an NLP AI analysis module for analyzing information retrieved upon querying said at least one subject-specific dataset and said at least one composite dataset, and
a report module which provides recommended further course(s) of action to said subject and/or initiates personalized health and wellness actions (e.g., scheduling an appointment, when warranted, with a physician, an urgent care center, a hospital emergency room, and the like).

Such apps can be employed using only one or more composite datasets; alternatively, such apps can further comprise one or more subject-specific datasets as well.

In accordance with a still further embodiment of the present invention, there are provided apps which facilitate user-interactive querying of:
  a plurality of composite datasets, and
  optionally, at least one subject-specific dataset
  for information relevant to a condition or objective of interest, said app comprising:
an NLP AI analysis module for analyzing information retrieved upon querying said at least one subject-specific dataset and said at least one composite dataset, and
a report module which provides recommended further course(s) of action to said subject and/or initiates personalized health and wellness actions (e.g., scheduling an appointment, when warranted, with a physician, an urgent care center, a hospital emergency room, and the like).

In certain aspects and embodiments, a plurality of composite datasets are employed; in certain aspects and embodiments, a plurality of subject-specific datasets are queried in addition to the plurality of composite datasets.

In some embodiments, one or more of the composite datasets are routinely updated and/or supplemented.

In some embodiments, one or more of the subject-specific datasets are routinely updated and/or supplemented.

In some embodiments, one or more datasets are added to the plurality of composite datasets.

In some embodiments, one or more datasets are added to the plurality of subject-specific datasets.

In some embodiments, the NLP AI analysis module of the above-described app instructs the app to automatically present to the subject user certain subsets of their personal, subject-specific dataset, when conditionally available in the health data vault, with knowledge or actionable recommendation(s) that are uniquely-tuned to the subject user.

In accordance with still another embodiment of the present invention, there are provided virtual primary care providers comprising:
  at least one composite dataset, and
  optionally, at least one subject-specific dataset
  a query module for retrieving information relevant to a condition or objective of interest from said datasets,
  an NLP AI analysis module for analyzing information retrieved upon querying said at least one subject-specific dataset and said at least one composite dataset, and
  a user-interactive reporter module which provides knowledge and/or recommended further course(s) of action to said subject.

In certain aspects and embodiments, the virtual primary care provider further comprises one or more subject-specific datasets, in addition to the required one or more composite datasets.

In certain aspects and embodiments, a plurality of composite datasets are employed; in certain aspects and embodiments, a plurality of subject-specific datasets are queried in addition to the plurality of composite datasets.

Virtual primary care providers contemplated herein are able to fulfill many of the functions of an MD, a chiropractor, a genetic counselor, a nurse, a health coach, a nutritionist, a personal trainer, and the like.

In accordance with yet another embodiment of the present invention, there are provided methods of generating a custom menu of meals/beverages/snacks for an individual, said method comprising:
  (a) querying:
    at least one composite dataset, and
    at least one subject-specific dataset
    for information relevant to a meal/beverage/snack of interest to said subject,
  (b) analyzing the information retrieved in the preceding step, and
  (c) generating a menu of options for consumption by said subject.

In accordance with yet another embodiment of the present invention, there are provided methods of generating a custom menu of meals/beverages/snacks for an individual, said method comprising:
(a) querying:
  a plurality of composite datasets, and
  optionally, at least one subject-specific dataset
  for information relevant to a meal/beverage/snack of interest to said subject,
(b) analyzing the information retrieved in the preceding step, and
(c) generating a menu of options for consumption by said subject. In accordance with yet another embodiment of the invention, there are provided methods of generating a notification based on recognition of a pattern for an individual, said method comprising:
(a) querying:
  at least two subject-specific datasets
  for information relevant to patterns in the user's activities and responses, such as symptoms reported after food intake
(b) analyzing the information retrieved in the preceding step, and
(c) generating a notification of patterns observed in the data associated with said subject.

In accordance with yet another embodiment of the invention, there are provided methods of generating a notification to a user's emergency contact, said method comprising:
(a) querying:
  at least two subject-specific datasets, at least one of which is user inputs;
  for signs of medical emergency
(b) analyzing the information retrieved in the preceding step,
(c) generating a prompt to the user to acknowledge their current status
(d) generating a prompt to the user's identified emergency contact in the event that the user does not respond to the prompt to the user of step c.

In certain embodiments, the invention also includes a rewards system where the user is given incentives, such as reduced insurance premiums, movie tickets, or other discounts for modifying their behavior in response to the recommendations generated.

In certain aspects and embodiments, a plurality of composite datasets are employed; in certain aspects and embodiments, at least one subject-specific dataset is queried in addition to the plurality of composite datasets.

The following examples are provided to further illustrate aspects of the invention. These examples are non-limiting and should not be construed as limiting any aspect of the invention.

EXAMPLE 1

Query of Exemplary Composite and Subject-Specific Datasets

Referring to FIG. 1, an exemplary query according to the present invention is carried out as follows:
1. Query 'Q' is entered by the user in natural human language on a mobile device, for example, "Where can I get a healthy dinner tonight?".
2. Q is received at the computer server, where subject-specific data 'L', such as lab-determined metabolism and nutrient responses, genetic phenotypes of the user, and the user's local zip code, are added to the modified query as Q'(L).
3. NLP AI "reads" Q'(L) and accesses both genetics science literature data set 'd1' and restaurant business data set 'd7' to form, along with a confidence-score, one or more answer hypotheses, A, such as:

"Mediterranean Bistro on 5th Street [GEO:–117.1221;+34.3242][PH:18585551234]"

which hypotheses are returned to the computer server, containing, in this example, embedded annotations for the restaurant location and phone number, recommending the optimal diet type for the user's body, and recommending a restaurant having a menu compatible with that diet type and nearby the user.
4. The computer server receives A and generates A'(C), which includes a mobile application command to open the map display feature centered on the restaurant and prompt the user with the restaurant's phone number and the option to call for a reservation.

This example demonstrates how the invention system addresses a simple inquiry by bringing to bear numerous general and subject-specific considerations.

EXAMPLE 2

Query of Additional Exemplary Composite and Subject-Specific Datasets

Referring to FIG. 1, an additional exemplary query according to the present invention is carried out as follows:
1. A user with a mobile device poses question Q: "How much should I expect to pay for a knee replacement?"
2. Q'(L): the computer server annotates Q with data L from V containing user location (zip code), age, sex, and other private data items.
3. NLP AI receives Q'(L), references dataset d19 for knee replacement cost at various hospitals and clinics which are in the geographic proximity of the user's zip code, generating, in this example, a single high-confidence answer A "Average price for knee replacement surgery in zip code 92121 is $17,000."
4. The computer server relays A as A'(C) to a mobile app, where C in this case causes the mobile app to simply display the answer to the mobile device user.

This example demonstrates another use of the invention system to synthesize available information so as to generate a recommendation of interest to the subject.

EXAMPLE 3

Query of Additional Exemplary Composite and Subject-Specific Datasets

Referring to FIG. 1, yet another exemplary query according to the present invention is carried out as follows:
1. A web user enters query Q: "My husband has no genetic carrier mutations. Will our children get sick with my mother's diseases?"
2. Q'(L) is assembled from Q and V where L includes the user's genetic lab phenotypes, the user's family medical history survey data such as the mother's cystic fibrosis disease diagnosis at age 27, and other data.

3. NLP AI references genomic mutations dataset d3, medical conditions dataset d5, science journals dataset d12, and determines two probable hypotheses for its answer A:
   Children of recessive single-carrier parents are highly unlikely to contract the carried disease. (85%); or
   Children have a 25% chance of contracting a genetic disease only when both parents are heterozygous (single strand) carriers of the same disease. (60%).

This example demonstrates that the invention system is useful for providing guidance such as genetic counseling.

EXAMPLE 4

Query of Additional Exemplary Composite and Subject-Specific Datasets

Referring to FIG. 1, an exemplary query according to the present invention is carried out as follows:
1. Query 'Q' is entered by the user in natural human language on a mobile device, for example, "thus far today, I have consumed the following . . . what menu options for dinner will provide me with optimal protein, carbohydrate and fat consumption?"
2. Q is received at the computer server, where subject-specific data 'L', such as genetic information, health information, food ingested during the day, zip codes to which the subject has easy access, and biometric data are added to the modified query as Q'(L).
3. NLP AI "reads" Q'(L) and references the composite database with respect to "Recommended food profile" (e.g., % protein-% fats-% carbs to be ingested each day—40% carbs-30% protein-30% fats) and "calculation of food profile ingested" (i.e., analysis of foods that if ingested would generate the preferred food profile) to form, along with a confidence-score, one or more answer hypotheses, A, such as "preferred menu items," restaurants which offer such recommended menu items in conveniently accessible proximity to the subject (e.g., sorted by zip code), and the like. The resulting recommendations are returned to the computer server, containing, in this example, embedded annotations for the restaurant location and phone number, recommending the optimal diet type for the user's body, and recommending a restaurant having a menu compatible with that diet type and nearby the user.
4. The computer server receives A and generates A'(C), which includes a mobile application command to open the map display feature centered on the restaurant and prompt the user with the restaurant's phone number and the option to call for a reservation.

This example demonstrates yet another use of the invention system to synthesize available information so as to generate a recommendation of interest to the subject.

EXAMPLE 5

Query of Additional Exemplary Composite and Subject-Specific Datasets

Referring to FIG. 1, an exemplary query according to the present invention is carried out as follows:
1. Query 'Q' is entered by the user in natural human language on a mobile device, for example, "what should my menu preferences be for today?"
2. Q is received at the computer server, where subject-specific data 'L', such as genetic information, health information, zip code, biometric data, food input and meals cooked at home are added to the modified query as Q'(L).
3. NLP AI "reads" Q'(L) and references the composite database for the information required to conduct a calculation of intake and energy expended, as well as a list of restaurants and menu items conveniently accessible to the subject, so as to form, along with a confidence-score, one or more answer hypotheses, A, such as "suggested meals to cook at home or a select number of local restaurants with appropriate menu items", which recommendations are returned to the computer server, containing, in this example, embedded annotations for the restaurant location and phone number, recommending the optimal diet type for the user's body, and recommending a restaurant having a menu compatible with that diet type and nearby the user.
4. The computer server receives A and generates A'(C), which includes a mobile application command to open the map display feature centered on the restaurant and prompt the user with the restaurant's phone number and the option to call for a reservation.

This example demonstrates still another use of the invention system to synthesize available information so as to generate a recommendation of interest to the subject.

EXAMPLE 6

Query of Additional Exemplary Composite and Subject-Specific Datasets

Referring to FIG. 1, an exemplary query according to the present invention is carried out as follows:
1. Query 'Q' is entered by the user in natural human language on a mobile device, for example, "What exercise(s) should I do today?".
2. Q is received at the computer server, where subject-specific data 'L', such as genetic information, health information, zip code, biometric data, food input, fitness club membership, and past exercise routines are added to the modified query as Q'(L).
3. NLP AI "reads" Q'(L) and references meteorological data, terrain/map data to form, along with a confidence-score, one or more answer hypotheses, A, such as "there is a high pollen count today; in-gym exercise is preferred"; or "here is a map for a proposed five mile run" which recommendations are returned to the computer server, containing, in this example, embedded annotations with details regarding the suggested running route; optionally including a recommendation regarding the optimal diet type for the user's body, and recommending a restaurant having a menu compatible with that diet type and nearby the user.
4. The computer server receives A and generates A'(C), which includes a mobile application command to open the map display feature centered on the restaurant and prompt the user with the restaurant's phone number and the option to call for a reservation.

This example demonstrates a further use of the invention system to synthesize available information so as to generate a recommendation of interest to the subject.

EXAMPLE 7

Query of Additional Exemplary Composite and Subject-Specific Datasets

Referring to FIG. 1, an exemplary query according to the present invention is carried out as follows:

1. Query 'Q' is entered by the user in natural human language on a mobile device, for example, "my hand is swollen, what should I do?"
2. Q is received at the computer server, where subject-specific data 'L', such as genetic information, health information, zip code, biometric data, insurance company information, exercise information, and occupation are added to the modified query as Q'(L).
3. NLP AI "reads" Q'(L) and references the composite database with respect to "medical literature" and "workplace injury", to form, along with a confidence-score, one or more answer hypotheses, A, such as "treatment options," "relief options," "recommended additional evaluations" (and conveniently accessible zip codes where such additional evaluations can be obtained), and the like. Such recommendations are returned to the computer server, containing, in this example, embedded annotations which facilitate pursuing one of the identified relief options, e.g., directions to the nearest medical facility with the capability of assisting with the suspected injury, wherein said medical facility is a participant in the subject's health-care plan.
4. The computer server receives A and generates A'(C), which includes a mobile application command to open the map display feature centered on the recommended medical facility and prompt the user with the phone number therefor, and the option to call for an appointment.

EXAMPLE 8

Query of Exemplary Composite and Subject-Specific Datasets

Referring to FIG. 1, an exemplary query according to the present invention is carried out as follows:
1. Query 'Q' is entered by the user in natural human language on a mobile device, for example, "who is the best heart doctor in La Jolla?"
2. Q is received at the computer server, where subject-specific data 'L', such as health information, zip code, biometric data, insurance company information, physician information such as physician specialty, physician location, physician contact information, number of patient visits to physician, insurance accepted by physician, and the like, are added to the modified query as Q'(L)
3. NLP AI "reads" Q'(L) and references the composite database with respect to "physician" and "cardiology", to form, along with a confidence-score, one or more answer hypotheses, A, such as "cardiologist options", "cardiologist reviews" and "recommended additional evaluations" (and conveniently available zip codes and contact information for such physicians), and the like. Such recommendations are returned to the computer server, containing, in this example, embedded annotations which facilitate pursuing one of the identified cardiologists, e.g., contact information, insurance accepted, directions to office, and the like.
4. The computer server receives A and generates A'(C), which includes a mobile application command to open the map display feature centered on the recommended physician office and prompt the user with the phone number therefor, and the option to call for an appointment.

This example demonstrates a further use of the invention system to synthesize available information so as to generate a recommendation of interest to the subject.

EXAMPLE 9

Query of Exemplary Composite and Subject-Specific Datasets

Referring to FIG. 1, an exemplary query according to the present invention is carried out as follows:
1. Query 'Q' is entered by the user in natural human language on a mobile device, for example, "where is the cheapest procedure for angioplasty?"
2. Q is received at the computer server, where subject-specific data 'L', such as health information, zip code, biometric data, insurance company information, medical center information such as number of procedures, average cost of procedures, insurance accepted by medical center, and the like, are added to the modified query as Q'(L).
3. NLP AI "reads" Q'(L) and references the composite database with respect to "medical treatment center", "cost" and "angioplasty", to form, along with a confidence-score, one or more answer hypotheses, A, such as "angioplasty procedure locations", "angioplasty cost" and "recommended additional evaluations" (and conveniently available zip codes and contact information for such physicians), and the like. Such recommendations are returned to the computer server, containing, in this example, embedded annotations which facilitate pursuing one of the identified medical centers, e.g., contact information, insurance accepted, directions to office, and the like.
4. The computer server receives A and generates A'(C), which includes a mobile application command to open the map display feature centered on the recommended medical center and prompt the user with the phone number therefor, and the option to call for an appointment.

This example demonstrates a further use of the invention system to synthesize available information so as to generate a recommendation of interest to the subject.

EXAMPLE 10

Query of Exemplary Composite and Subject-Specific Datasets

Referring to FIG. 1, an exemplary query according to the present invention is carried out as follows:
1. Query 'Q' is entered by the user in natural human language on a mobile device, for example, "does my insurance cover orthopedic surgery?"
2. Q'(L): the computer server annotates Q with data L from V containing user location (zip code), age, sex, insurance coverage information, and the like, such as, for example, other private data items.
3. NLP AI "reads" Q'(L) and references insurance coverage dataset for coverage as well as hospitals and clinics covered by insurance which are in a geographic proximity of the user's zip code, generating, in this example, a single high-confidence answer A: "Your insurance does cover orthopedic surgery so long as medical necessity is established. You will be required to pay a co-insurance amount of 20%. [NAME] Medical Center is the closest center to your zip code that is covered by your insurance and that performs orthopedic surgery."
4. The computer server receives A and generates A'(C), which, in the event that orthopedic surgery is covered by the patients insurance, includes a mobile application command to open the map display feature centered on the recommended orthopedic surgery center and prompt the user with the phone number of the insurance company, and the option to call for confirmation of coverage.

This example demonstrates a further use of the invention system to synthesize available information so as to generate a recommendation of interest to the subject.

EXAMPLE 11

Query of Exemplary Composite and Subject-Specific Datasets

Referring to FIG. 1, an exemplary query according to the present invention is carried out as follows:
1. Query 'Q' is entered by the user in natural human language on a mobile device, for example, "what can I do for my headache?"
2. Q is received at the computer server, where subject-specific data 'L', such as health information, zip code, biometric data, medications taken by patient, medication interactions data are added to the modified query as Q'(L)
3. NLP AI "reads" Q'(L) and references the composite database with respect to "medical literature", "headache", to form, along with a confidence-score, one or more answer hypotheses, A, such as "treatment options", "relief options", drug interactions" and "recommended additional evaluations" (and conveniently available zip codes and contact information for such physicians), and the like. Such recommendations are returned to the computer server, containing, in this example, embedded annotations which facilitate pursuing one of the identified treatment options, e.g., contact information for nearby pharmacy, information for online vendor, and the like.
4. The computer server receives A and generates A'(C), which includes a mobile application command to open the map display feature centered on the recommended pharmacy and prompt the user with a website, such as amazon.com, where the user may order, online, the necessary medication, such as ibuprofen.

This example demonstrates a further use of the invention system to synthesize available information so as to generate a recommendation of interest to the subject.

EXAMPLE 12

Query of Exemplary Composite and Subject-Specific Datasets

Referring to FIG. 1, an exemplary query according to the present invention is carried out as follows:
1. Query 'Q' is entered by the user in natural human language on a mobile device, for example, "I have a runny nose and a fever, and very low appetite. I am also queasy. What should I do?"
2. Q is received at the computer server, where subject-specific data 'L', such as health information, zip code, biometric data, medications taken by patient, medication interactions data, and the like, are added to the modified query as Q'(L)
3. NLP AI "reads" Q'(L) and references the composite database with respect to "medical literature", "symptom checker", to form, along with a confidence-score, one or more answer hypotheses, A, such as "treatment options", "relief options", drug interactions" and "recommended additional evaluations" (and conveniently available zip codes and contact information for such physicians), and the like. Such recommendations are returned to the computer server, containing, in this example, embedded annotations which facilitate pursuing one of the identified potential illnesses, such as influenza, treatment options, e.g., contact information for nearby pharmacy.
4. The computer server receives A and generates A'(C), which includes a mobile application command to open the map display feature centered on the recommended pharmacy and prompt the user with a website, such as amazon.com, where the user may order, online, the recommended treatment items, such as an electrolyte drink for hydration.
5. In some instances, the system may request additional information from the user, for example "What is your current temperature?"

This example demonstrates a further use of the invention system to synthesize available information so as to generate a recommendation of interest to the subject.

EXAMPLE 13

Query of Exemplary Composite and Subject-Specific Datasets

Referring to FIG. 1, an exemplary query according to the present invention is carried out as follows:
1. Query 'Q' is entered by the user in natural human language on a mobile device, for example, "can you remind me when to take my Topomax?"
2. Q'(L): the computer server annotates Q with data L from V containing user location (zip code), age, sex, prescription information, and the like, such as other private data items.
3. NLP AI "reads" Q'(L) and references patient specific prescription dataset as well as medical literature on drug interactions, generating, in this example, a single high-confidence answer A: "You need to take your Topomax twice daily. You should take your next dose at 6 pm. Topomax may interact with alcohol and can cause excessive sleep, confusion and difficulty with memory or speech."
4. The computer server receives A and generates A'(C), which includes a mobile application command to open the calendar function with an option to set a calendar reminder for twice a day.

This example demonstrates a further use of the invention system to synthesize available information so as to generate a recommendation of interest to the subject.

EXAMPLE 14

Query of Exemplary Composite and Subject-Specific Datasets

Referring to FIG. 1, an exemplary query according to the present invention is carried out as follows:
1. Query 'Q' is entered by the user in natural human language on a mobile device, for example, "I am a diabetic and I've eaten pasta. When should I take my next shot of insulin?"
2. Q'(L): the computer server annotates Q with data L from V containing user location (zip code), age, sex, prescription information, and the like, such as other private data items.
3. NLP AI "reads" Q'(L) and references patient specific prescription dataset as well as medical literature on insulin, generating, in this example, a single high-confidence answer A: "You are next scheduled to take your [User_RX_name, ex: Humulin] on [User_RX_Next_DateTime, ex: Monday at 3 pm]."
4. The computer server receives A and generates A'(C), which includes a mobile application command to open the map display feature centered on the pharmacy most recently used to refill the user's prescription for insulin, prompt the user with the phone number of the pharmacy, and the option to call for a refill.

This example demonstrates a further use of the invention system to synthesize available information so as to generate a recommendation of interest to the subject.

EXAMPLE 15

Query of Exemplary Composite and Subject-Specific Datasets

Referring to FIG. 1, an exemplary query according to the present invention is carried out as follows:
1. Query 'Q' is entered by the user in natural human language on a mobile device, for example, "what kind of vitamin should I take while pregnant?"
2. Q'(L): the computer server annotates Q with data L from V containing user location (zip code), age, prescription information, and the like, such as other private data items.
3. NLP AI "reads" Q'(L) and references patient specific prescription dataset as well as medical literature on vitamins and pregnancy, generating, in this example, a single high-confidence answer A: "Based on your genetics and medical history, you should be able to take most common prenatal vitamins. Look for a prenatal vitamin that includes:
   400 micrograms (mcg) of folic acid,
   400 IU of vitamin D,
   200 to 300 milligrams (mg) of calcium,
   70 mg of vitamin C,
   3 mg of thiamine,
   2 mg of riboflavin,
   20 mg of niacin,
   6 mcg of vitamin B12,
   10 mg of vitamin E,
   15 mg of zinc,
   17 mg of iron, and
   150 micrograms of iodine."
4. The computer server receives A and generates A'(C), which includes a mobile application command to open the map feature centered on a pharmacy or drug store in the user's zip code that carries the recommended vitamins.

This example demonstrates a further use of the invention system to synthesize available information so as to generate a recommendation of interest to the subject.

EXAMPLE 16

Query of Exemplary Composite and Subject-Specific Datasets

Referring to FIG. 1, an exemplary query according to the present invention is carried out as follows:
1. Query 'Q' is entered by the user in natural human language on a mobile device, for example, "What are the results of my genetic test?"
2. Q'(L): the computer server annotates Q with data L from V containing results of the user's genetic testing, age, sex, biometric data, and the like, such as other private data items.
3. NLP AI "reads" Q'(L) and references patient specific genetic test result dataset, generating, in this example, a single high-confidence answer A: "Most of your results are unremarkable, except for your result for Asthma which shows that you have an above average risk for asthma. Would you like to learn more?"
4. The computer server receives A and generates A'(C), which includes a mobile application command to open the web browser to a webpage with more information on Asthma.

This example demonstrates a further use of the invention system to synthesize available information so as to generate a recommendation of interest to the subject.

EXAMPLE 17

Query of Exemplary Composite and Subject-Specific Datasets

Referring to FIG. 1, an exemplary query according to the present invention is carried out as follows:
1. Query 'Q' is entered by the user in natural human language on a mobile device, for example, "What are my current health concerns?"
2. Q'(L): the computer server annotates Q with data L from V containing results of the user's genetic testing, age, sex, biometric data, and the like, such as other private data items.
3. NLP AI "reads" Q'(L) and references patient specific genetic test result dataset, generating, in this example, a single high-confidence answer A: "Your overall health condition is good. Items that you need to be aware of include: increased cholesterol level. Do you want to consult your physician?"
4. The computer server receives A and generates A'(C), which includes a mobile application command to open the map display feature centered on the user's primary physician's office and prompt the user with the phone number of the physician.

This example demonstrates a further use of the invention system to synthesize available information so as to generate a recommendation of interest to the subject.

The preceding examples demonstrate numerous uses contemplated for the invention system to synthesize available information so as to generate a recommendation of interest to the subject, and/or initiating personalized health and wellness actions (e.g., scheduling an appointment, when warranted, with a physician, an urgent care center, a hospital emergency room, and the like).

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

What is claimed is:

1. A method of managing health and wellness of a subject, the method comprising
   (a) inputting a subject-specific query related to personalized health and wellness management into a Natural Language Processing Artificial Intelligence (NLP AI) analysis module of a personalized health and wellness management system, the personalized health and wellness management system comprising:
      a plurality of composite datasets, collectively comprising scientifically-curated genetics-related information, nutritional data, exercise data, and food and activity data;
      a plurality of subject-specific datasets, collectively comprising subject-specific genomic information, subject-specific phenotypic information, and subject-specific exercise information;
      the NLP AI analysis module comprising a hardware processor;
      stored program code executable by said analysis module or the hardware processor thereof; and
      a report module that produces a report comprising a recommended personalized health and wellness action,
   wherein:
      the analysis module is communicatively coupled to the plurality of composite datasets, the plurality of subject-specific datasets, and the report module;
      the stored program code configures the analysis module, in response to a subject-specific query related to personalized health and wellness management, to:
         query one or more of the plurality of composite datasets and one or more of the plurality of subject-specific datasets for information related to the subject-specific query and identify the information related to the subject-specific query;
         produce an output based on the information related to the subject-specific query and communicates the output to the reporter module; and
         produce a report via the reporter module, the report comprising a recommended personalized health and wellness action responsive to the subject-specific query and based on:
            the subject-specific genomic information and one or more of the subject-specific phenotypic information and the subject-specific exercise information; and
            the scientifically-curated genetics-related information and one or more of the nutritional data, the exercise data, and the food and activity data;
   (b) querying, via the analysis module, the plurality of composite datasets and the plurality of subject-specific datasets to identify the information related to the subject-specific query;
   (c) producing, via the analysis module, the output based on the information related to the subject-specific query;
   (d) communicating the output to the reporter module; and
   (e) generating, via the reporter module, the report comprising a recommended personalized health and wellness action responsive to the subject-specific query and based on:
      the subject-specific genomic information and one or more of the subject-specific phenotypic information and the subject-specific exercise information; and
      the scientifically-curated genetics-related information and one or more of the nutritional data, the exercise data, and the food and activity data,
   wherein the information retrieved in the querying step is analyzed by Natural Language Processing Artificial Intelligence (NLP AI) which operates upon the composite and subject-specific datasets to generate multiple hypotheses for both the natural human meaning of the query and answers to the query, and presents in descending sorted-order one or more confidence-scored answers extracted from the unstructured data, wherein the NLP AI has been trained by one or more subject-matter experts selected from the group consisting of scientists, doctors, researchers, and clinicians, or the NLP AI is trained directly by the subject, and wherein the NLP AI may be queried either with the context of the subject-specific dataset, or without it, and where the subject-specific dataset is automatically maintained within the user's personal data vault;

the subject-specific dataset is automatically updated within the user's personal data vault, or may be manually updated with specific data transmitted directly from, or indirectly by authorized persons, with data from newly-released clinical laboratory test(s), new or user-edited in-application chat log text entries, new medical records, medical information and/or user preference information; and the contextual information of the subject-specific dataset modifies with additional specificity and accuracy the response knowledge or actionable recommendations generated by the NLP AI.

2. The method of claim 1 wherein said query is a written and/or spoken query, wherein some written questions are auto-generated by the method to guide the user's line of inquiry toward a specific answer; and wherein said auto-generated questions are presented as touch-to-ask-this questions.

3. The method of claim 1 wherein said query is user-interactive.

4. The method of claim 1 wherein said subject-specific datasets and said composite datasets are routinely updated.

* * * * *